United States Patent
Hui et al.

(10) Patent No.: US 7,656,999 B2
(45) Date of Patent: *Feb. 2, 2010

(54) RADIOTHERAPY DEVICE

(75) Inventors: Xiaobing Hui, Shenzhen (CN); Shiqun Xiao, Shenzhen (CN); Jian Huang, Shenzhen (CN)

(73) Assignee: Shenzhen Hyper Technology Incorporation, Futian District, Shenzhen, Guangdong (CN)

( * ) Notice: Subject to any disclaimer, the term of this patent is extended or adjusted under 35 U.S.C. 154(b) by 169 days.

This patent is subject to a terminal disclaimer.

(21) Appl. No.: 11/817,356

(22) PCT Filed: Jul. 3, 2006

(86) PCT No.: PCT/CN2006/001539

§ 371 (c)(1), (2), (4) Date: Aug. 29, 2007

(87) PCT Pub. No.: WO2007/022679

PCT Pub. Date: Mar. 1, 2007

(65) Prior Publication Data

US 2009/0086909 A1    Apr. 2, 2009

(30) Foreign Application Priority Data

Aug. 25, 2005   (CN) .......................... 2005 1 0036679

(51) Int. Cl.
*A61N 5/10* (2006.01)

(52) U.S. Cl. .......................... 378/65; 378/147; 378/193

(58) Field of Classification Search ..................... 378/9, 378/10, 65, 147, 149, 62, 64, 145, 193–198
See application file for complete search history.

(56) References Cited

U.S. PATENT DOCUMENTS

| 6,512,813 | B1* | 1/2003 | Krispel et al. ................. 378/65 |
| 2004/0005027 | A1* | 1/2004 | Nafstadius .................... 378/65 |

* cited by examiner

*Primary Examiner*—Courtney Thomas
(74) *Attorney, Agent, or Firm*—Global IP Services; Tianhua Gu

(57) ABSTRACT

The invention involves a rotary focused gamma-ray radiotherapy device. The invention includes a frame, a rotary ring positioned at the frame, and a source carrier and a collimator carrier that can rotate around a rotary axis respectively. The source carrier is equipped inside with multiple radiation sources. The collimator carrier is equipped inside with a corresponding beam channel to the radiation sources, which focus at a shared focus of the rotary axis through the beam channel. The source carrier and the collimator carrier are connected at both ends with the rotary ring and the frame, respectively. The single-layer and double-support structure of the source carrier and the collimator carrier adopted in the invention enlarges the treatment space, lowers manufacturing cost and difficulty, simplifies the mechanical structure, increases support rigidity of the source carrier and the collimator carrier, ensuring long-lasting and steady coaxial rotation of source carrier and collimator carrier, as well as position accuracy of the focusing center in the therapeutic system. Therefore, a precision radiotherapy is realized with improved radiotherapy effect.

11 Claims, 9 Drawing Sheets

RADIOTHERAPY DEVICE

FIELD OF THE INVENTION

The invention involves a medical radiotherapy device, i.e., a rotary focused gamma-ray radiotherapy device particularly.

BACKGROUND OF THE INVENTION

The radiotherapy using a radiotherapy device, is to make the patient's targets rotatively irradiated as per the work principle of rotation focusing, with the target tissues at the rotary focus subjected to the maximum dose of radiation while the healthy tissues to an instantaneous tolerable dose of radiation, so as to kill the targets while sparing the surrounding healthy tissues. As a result, the aim of radiotherapy can be achieved. A radiotherapy device is disclosed in the patent of multi-source whole-body radiotherapy device with Chinese Patent Publication Number CN 1275410. The radiotherapy device includes a source carrier, a rotary ring fixed to the source carrier, a collimator carrier, a rotary ring fixed to the collimator carrier, a rotary support, and a fixed rotary support ring. Multiple rolling bearings are positioned between the rotary support ring and the rotary ring of the source carrier, as well as between the rotary ring of the source carrier and that of the collimator carrier respectively, forming a rotary fit with axial localization. The source carrier and the collimator carrier can rotate around the same rotary axis respectively, and multiple radiation sources distributed in the source carrier irradiate on a shared focus at the rotary axis through radiation channel in the source carrier and the collimator carrier. The collimator carrier is equipped with collimators, divided into groups as per different apertures. The collimators of each group are distributed in the same way as the radiation sources in the source carrier. The radiation sources and the radiation channel in the source carrier are distributed radially in a sectorial area with angle of less than 90 degrees, and axially in a sectorial area with angle of less than 60 degrees. The interior rotary radius of the collimator carrier is 56 cm, smaller than the human body width. The diameter of the collimator carrier rotary ring is 1 m.

The rotary support of the above-mentioned device is equipped inside with the rotary support ring, the rotary ring of the source carrier and of the collimator carrier. Its shortcomings are that the three inlaid slip-on rotary rings reduce the treatment space and the rotary scope of the collimator carrier, and increase manufacturing difficulty and cost; and with the source carrier and the collimator carrier connected at both ends with the rotary support through the rotary ring, whose minimum diameter is 1 m, the bigger rotary ring of the source carrier and of the collimator carrier as well as complicated manufacturing process, affect the coaxial rotation accuracy of the source carrier and of the collimator carrier during rotary focusing of the radiation beam, thus affecting the focusing accuracy of the radiation beam from the sources and lowering the radiotherapy effect.

SUMMARY OF THE INVENTION

The invention is to provide a radiotherapy device. It's to technically enlarge the treatment space, lower manufacturing difficulty and cost, and improve the radiotherapy accuracy.

The invention adopts the following technical solutions in order to achieve the above: A radiotherapy device includes a frame, a rotary ring fixed at the frame, a source carrier and a collimator carrier that can rotate respectively around the rotary axis. The source carrier is equipped inside with multiple radiation sources. The collimator carrier is equipped inside with a corresponding beam channel to the radiation sources. The radiation sources through the beam channel focus on the radiation focus at the rotary axis. The source carrier and the collimator carrier are connected at both ends with the rotary ring and the frame respectively.

One end of the source carrier and of the collimator carrier is fixed at the rotary ring of the source carrier and of the collimator carrier, while the other end movably connected with the frame through or not through a slip ring. The rotary ring of the source carrier and that of the collimator carrier are coaxially positioned on both sides of the radiation focus at the rotary axis, with their rotary axes coincident with each other. The rotary ring is equipped with a gear, connected to a power drive mechanism.

The radiotherapy device also includes a diagnostic imaging system, consisting of diagnostic radiation sources, a detector and a data processing system. The diagnostic radiation sources and the detector are installed respectively either at the source carrier and the rotary ring of it, or at the collimator carrier and the rotary ring of it. The detector is positioned oppositely to the diagnostic radiation sources along the rotary axis. The data processing system is connected with the detector, providing a related image as per information from the detector.

The diagnostic radiation sources are both cylindrical single-photon imaging sources and low activity cobalt-60 radiation sources.

The detector is connected with the rotary ring through a lever mechanism, able to move along the beam direction of the diagnostic radiation sources.

The invention has the following characteristics compared to the existing technology: The source carrier and the collimator carrier are connected at both ends with the rotary ring and the frame respectively. The single-layer and double-support structure of the invention, compared to the existing double-rotary-ring and double-support structure, enlarges the interior scope of the rotary ring, enlarges the treatment space helped by larger movement scope of treatment couch in the rotary ring, and lowers device manufacturing cost and difficulty. The source carrier and the collimator carrier are connected respectively at one end with the frame, thus simplifying the mechanical structure, reducing materials and weight, increasing support rigidity of the source carrier and the collimator carrier, making the manufacturing process simpler and more reliable and ensuring long-lasting and steady coaxial rotation of the source carrier and the collimator carrier. So the beam of the radiation sources in the source carrier can focus accurately through the beam channel in the collimator carrier, ensuring stability of the dose field distribution at the focusing center and position accuracy of the focusing center in treatment system. Therefore, a precision radiotherapy is realized with improved effect.

In the figures: 1. Radiation Focus; 2. Rotary Axis; 3. Frame; 4. Treatment couch; 10. Source Carrier; 11. Treatment Radiation sources; 12. Rotary Ring of Source Carrier; 13. Joint Piece of Source Carrier; 14. Source Box; 20. Collimator Carrier; 21. Collimator; 22. Rotary Ring of Collimator Carrier; 23. Joint Pin of Collimator Carrier; 30. Diagnostic Radiation sources; 31. Detector; 32. Lever Mechanism; 33. Preamplifier; 34. Data Converter; 35. Data Processor; 36. Gamma-Knife TPS System; 37. Control System of Gamma Knife; 100. Actuating device of Source Carrier; 101. Transmission Piece of Source Carrier; 200. Actuating device of Collimator Carrier; 201. Transmission Piece of Collimator Carrier.

DETAILED DESCRIPTION OF THE EMBODIMENTS

Further description would be given below in detail with the help of attached figures in embodiments.

Figure 1:
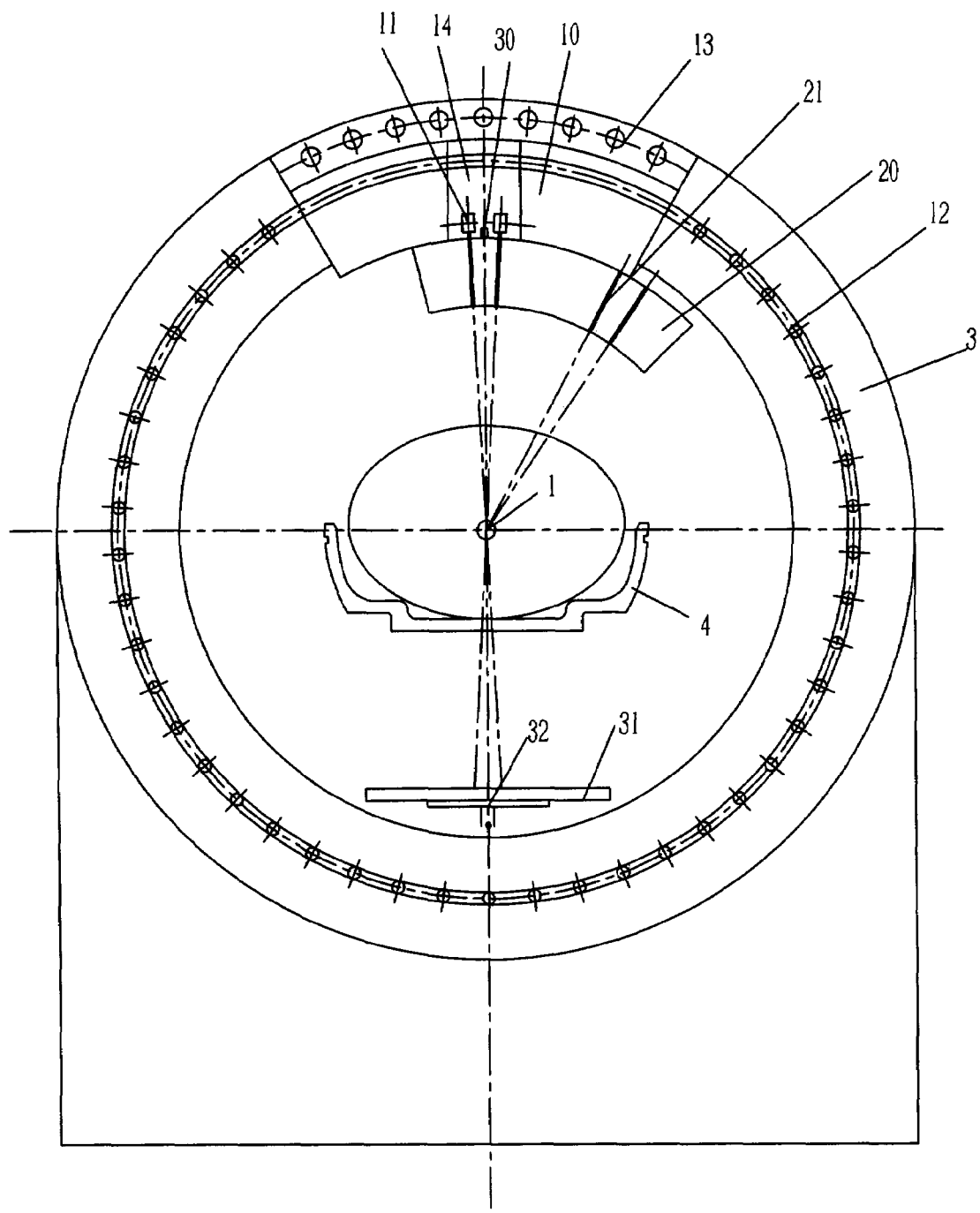
FIG. 1 is an overall structural diagram of the invention under a therapeutic state.
Figure 2:
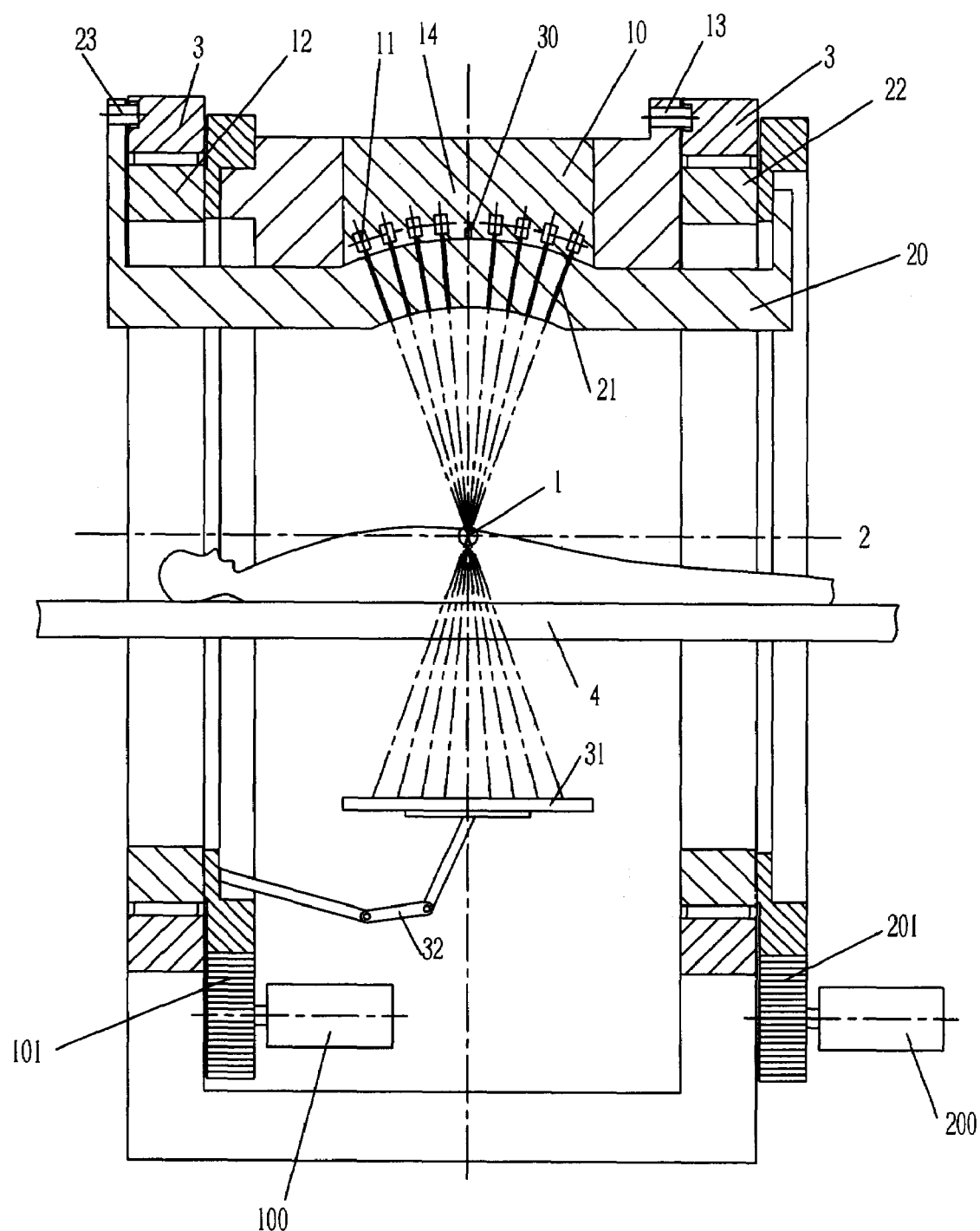
FIG. 2 is a sectional view of FIG. 1.
Figure 3:
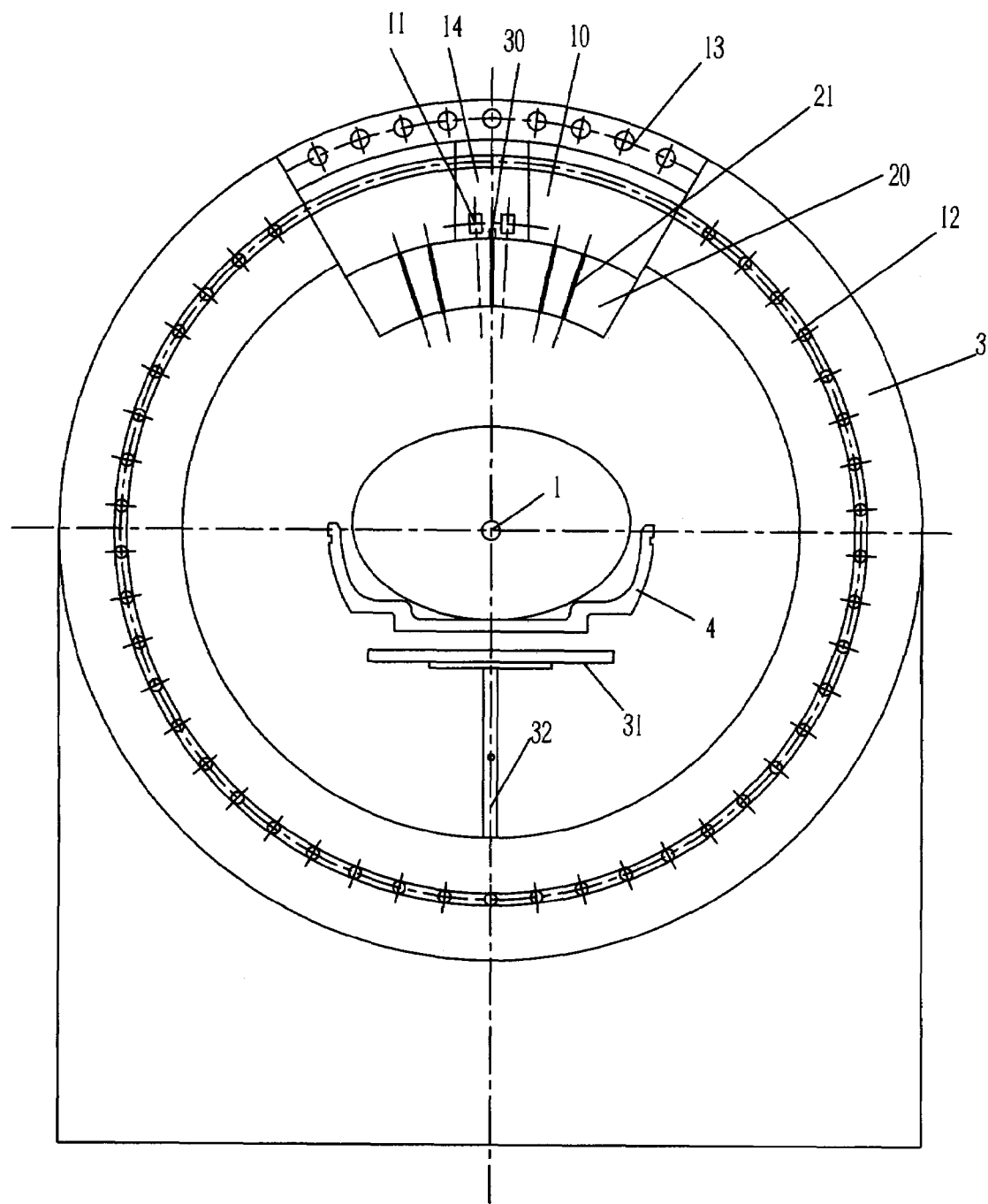
FIG. 3 is an overall structural diagram of the invention under an imaging state.

As shown in FIGS. 1 to 3, the imaging device of the radiotherapy system in an embodiment of the invention includes a frame 3, rotary ring 12 and 22 positioned at the frame, and a source carrier 10 and a collimator carrier 20 that can rotate around the rotary axis 2 respectively. The source carrier 10 is equipped inside with a source box 14, with multiple radiation sources 11 and 30 loaded inside. The collimator carrier is equipped inside with multiple groups of collimators 21 corresponding to the radiation sources. A beam channel is formed in the inner cavity of the collimator 21, through which the radiation sources focus at a radiation focus 1 of the rotary axis. One end of the source carrier 10 is fixed at the rotary ring 12 of the source carrier, while the other end is equipped with a convex block or a joint piece 13 of the source carrier. One end of the collimator carrier 20 is fixed at the rotary ring 22 of the collimator carrier, while the other end is equipped with a convex block or a joint piece 23 of the collimator carrier. The frame 3 is equipped on both sides of the radiation focus 1 with annular grooves, which receive the convex block or the joint piece 13 of the source carrier at one end of the source carrier 10 as well as the convex block or the joint piece 23 of the collimator carrier at one end of the collimator carrier 20, respectively. The convex block can be fitted by slide to the groove in the frame 3. The joint pieces 13 and 23 are multiple evenly-distributed cylinders, which can be fitted by rolling to the groove in the frame 3. The rotary ring 12 of the source carrier and the rotary ring 22 of the collimator carrier are coaxially positioned on both sides of the radiation focus 1 at the rotary axis 2, with their rotary axis 2 coincident with each other. The rotary ring is equipped with outer gears, which at the rotary ring 12 of the source carrier is connected with an actuating device 100 of the source carrier through a transmission piece 101 of the source carrier, and which at the rotary ring 22 of the collimator carrier is connected with an actuating device 200 of the collimator carrier through a transmission piece 201 of the collimator carrier. Rolling bearings are equipped between the rotary ring 12 of the source carrier and the frame 3 as well as between the rotary ring 22 of the collimator carrier and the frame 3, respectively, forming a rotary fit with an axial localization. The treatment couch 4, along the rotary axis 2, passes through the rotary ring 12 of the source carrier and the rotary ring 22 of the collimator carrier.

The source carrier 10 and the collimator carrier 20 of the invention are connected at both ends with the rotary ring 12 and 22 as well as the frame 3, respectively. This single-layer and double-support structure enlarges the interior scope of the rotary ring, enlarges the treatment space helped by larger movement scope of a treatment couch in the rotary ring, simplifies the mechanical structure, reduces materials and weight, increases support rigidity of the source carrier 10 and the collimator carrier 20, and lowers manufacturing cost and difficulty, makes the manufacturing process simpler and more reliable and ensures long-lasting and steady coaxial rotation of the source carrier and the collimator carrier. So the beam of the radiation sources in the source carrier 10 can focus accurately through the beam channel in the collimator carrier 20, ensuring stability of the dose field distribution at the focusing center and position accuracy of the focusing center in treatment system. Therefore, a precision radiotherapy is realized with improved effect.

The radiotherapy device also includes a diagnostic imaging system, consisting of diagnostic radiation sources 30, a detector 31 and a data processing system. The data processing system contains a preamplifier 33, a data converter 34, and a data processor 35. The diagnostic radiation sources 30 are both cylindrical single-photon imaging sources and low activity cobalt-60 radiation sources, being positioned in the source box 14 of the source carrier 10, and positioning the diagnostic radiation sources 31 at the center of the source carrier 10. The detector 31 is connected with the rotary ring 12 of the source carrier through a lever mechanism 32, which can move to a diagnostic site close to the treatment couch 4 or move to a therapeutic site away from the treatment couch 4 along the beam direction of the diagnostic radiation sources 30. The detector 31 is positioned oppositely to the source carrier 10 along the rotary axis 2 and, driven by the actuating device 100 of the source carrier, rotates step by step or continuously around the rotary axis 2 together with the source carrier 10. The diagnostic radiation sources 30 can also be installed at the center of the collimator carrier 20. Meanwhile, the detector 31 is connected with the rotary ring 22 of the collimator carrier through the lever mechanism 32 and, driven by the actuating device 200 of the collimator carrier, rotates step by step or continuously around the rotary axis 2 together with the collimator carrier 20. The detector 31 is positioned oppositely to the diagnostic radiation sources 30 along the rotary axis, and through the lever mechanism 32 at the rotary ring, can move to a diagnostic site close to the treatment couch 4 or move to a therapeutic site away from the treatment couch 4 along the beam of the diagnostic radiation sources 30.

Figure 9:
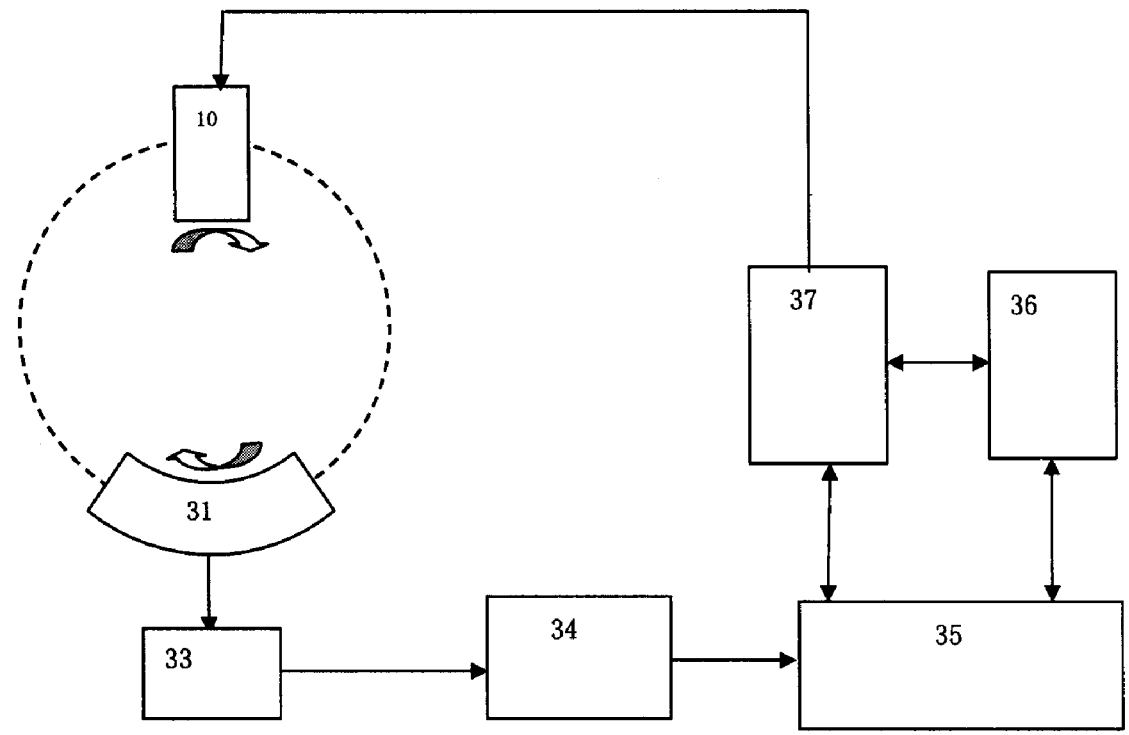
FIG. 9 is an imaging system structural block diagram of the invention.

As shown in FIG. 9, the detector 31 can receive radiation from both the diagnostic radiation sources 30 and the therapeutic radiation sources 11, and transmit information to the preamplifier 33 in the data processing system, respectively. The amplified radiation information is transmitted from the preamplifier 33 to the data converter 34 and, after data conversion, outputted to the data processor 35, which provides related images and information for a gamma-knife TPS system 36 and a gamma knife control system 37 as per received information. Pixel unit of the detector is 1 $mm^2$. When receiving radiation from the diagnostic radiation sources 30, the Cone-Beam CT method is adopted to image the patient's target areas, and Radon conversion and filtering rear-projection methods are adopted to acquire the corresponding CT-value density distribution and sectional images as well as position coordinates of the target areas and marker point, so as to confirm and adjust the patient's position. When receiving radiation from the radiation sources 11, the detector array obtains dose (transmission dose and scattering dose) distribution of the radiation sources 11 beam penetrating into the human carrier and, by the patient's CT-value density distribution obtained before therapy and the deconvolution method, reconstructs the patient's dose field distribution, i.e., a dose distribution of the actual radiation, of the target area and key tissues. Because physiological movement and non-automatic movement occur in the patient's target areas, especially in body parts such as chest, lung, liver, bowel, kidney and prostate gland, the coordinate positions of the target areas are changeable in the therapeutic device during treatment. Radiation dose and distribution actually obtained at the target area can be figured out approximately as per the position change and the dose distribution actually measured. A dose revision plan can be made in comparison with the TPS planned dose for the patient's supplementary radiation. Meanwhile, one can adopt a simplified algorithm, to perform a real-time monitoring and reconstruct a fractional dose (such as the radiation dose for each round), and compare with the planned fractional dose diagram, so as to present a real-time dose deviation and dose correction plan, and realize real-time monitoring and dynamic adjustment of the gamma knife dose radiation.

The radiotherapy device is an integration of a gamma-ray imaging system and a radiotherapy system. The data processing system integrates core contents of such corresponding items as images, tracking and dose reconstruction, performs data processing respectively, and provides such data acquisition functions as projection scanning, characteristic point tracking, and penetration dose measurement, so as to acquire desired monitoring results and correction data and realize real-time monitoring, verification and calibration.

As shown in FIGS. 1 and 2, when the radiotherapy device is under a therapeutic state, the actuating device 200 of the collimator carrier, through the transmission piece 201 of the collimator carrier, drives the rotary ring 22 of the collimator carrier to rotate around the rotary axis 2. The collimator carrier 20 rotates an angle relative to the source carrier 10, so that a group of the collimators 21 in the collimator carrier 20 fixed at the rotary ring 22 of the collimator carrier corresponds to the radiation sources 11 in the source carrier 10. The beam in the radiation sources 11, through the beam channel in the collimator 21, focuses at the radiation focus 1 of the rotary axis 2 and, through the patient on the treatment couch 4, irradiates on the detector 31. The detector 31, through the lever mechanism 32 connected with the rotary ring 12, is positioned at a therapeutic site away from the treatment couch 4. Driven by the actuating device 100 of the source carrier and the actuating device 200 of the collimator carrier, the source carrier 10, the collimator carrier 20, and the detector 31 together rotate continuously around the rotary axis 2.

As shown in FIG. 3, when the radiotherapy device is under an imaging state, the cylindrical single-photon diagnostic radiation sources 30 at the center of the source carrier 10, through an inner cavity channel of the collimator carrier at the center of the collimator carrier 20, penetrate into the patient on the treatment couch 4, and irradiate on the detector 31. The detector 31, through the lever mechanism 32 connected with the rotary ring 12, is positioned at a diagnostic site close to the treatment couch 4. Driven by the actuating device 100 of the source carrier and the actuating device 200 of the collimator carrier, the source carrier 10, the collimator carrier 20, and the detector 31 together rotate around the rotary axis 2 step by step.

Figure 4:
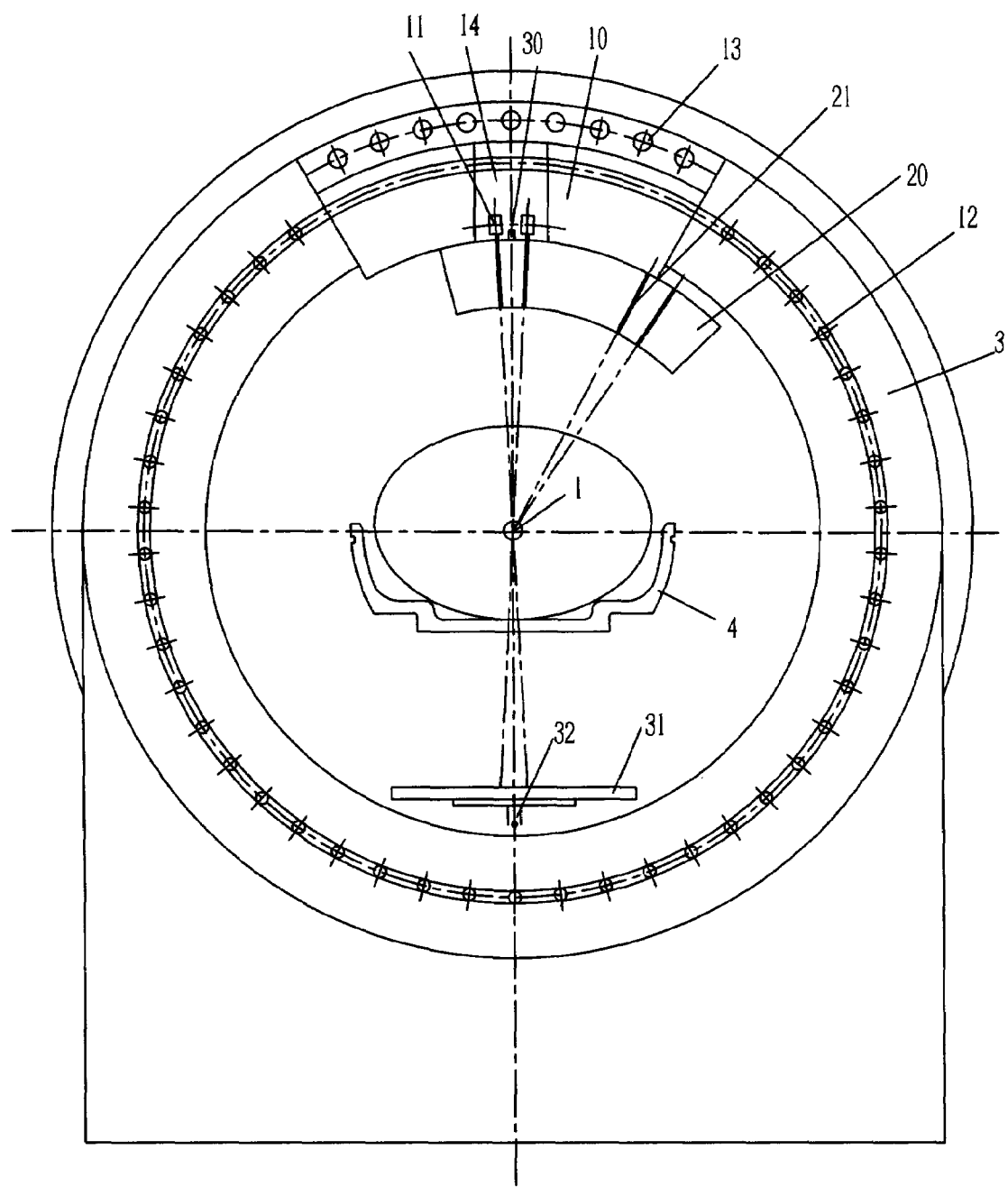
FIG. 4 is an overall structural diagram of the invention under a therapeutic state in second embodiment.
Figure 5:
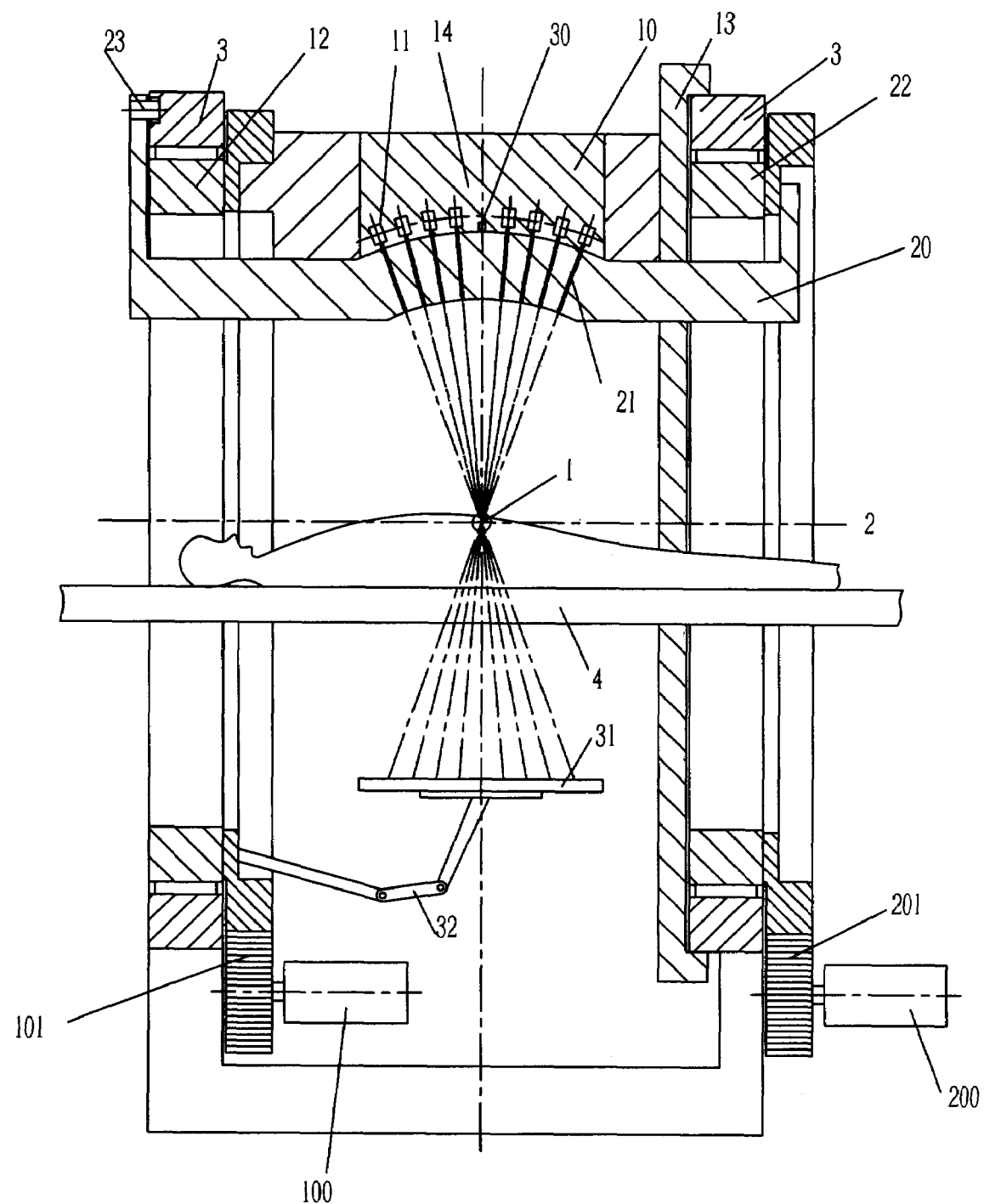
FIG. 5 is a sectional view of FIG. 4.

The second embodiment of the invention is as shown in FIGS. 4 and 5. One end of the source carrier 10 is fixed at the rotary ring 12 of the source carrier, while the other end at the joint piece 13 of the source carrier. The joint piece 13 of the source carrier has a ring-form structure with a concave surface, whose inner ring is fitted by slide to the outer surface of one end of the frame 3. Other structural characteristics of this embodiment are same as those of the first embodiment of the invention.

Figure 6:
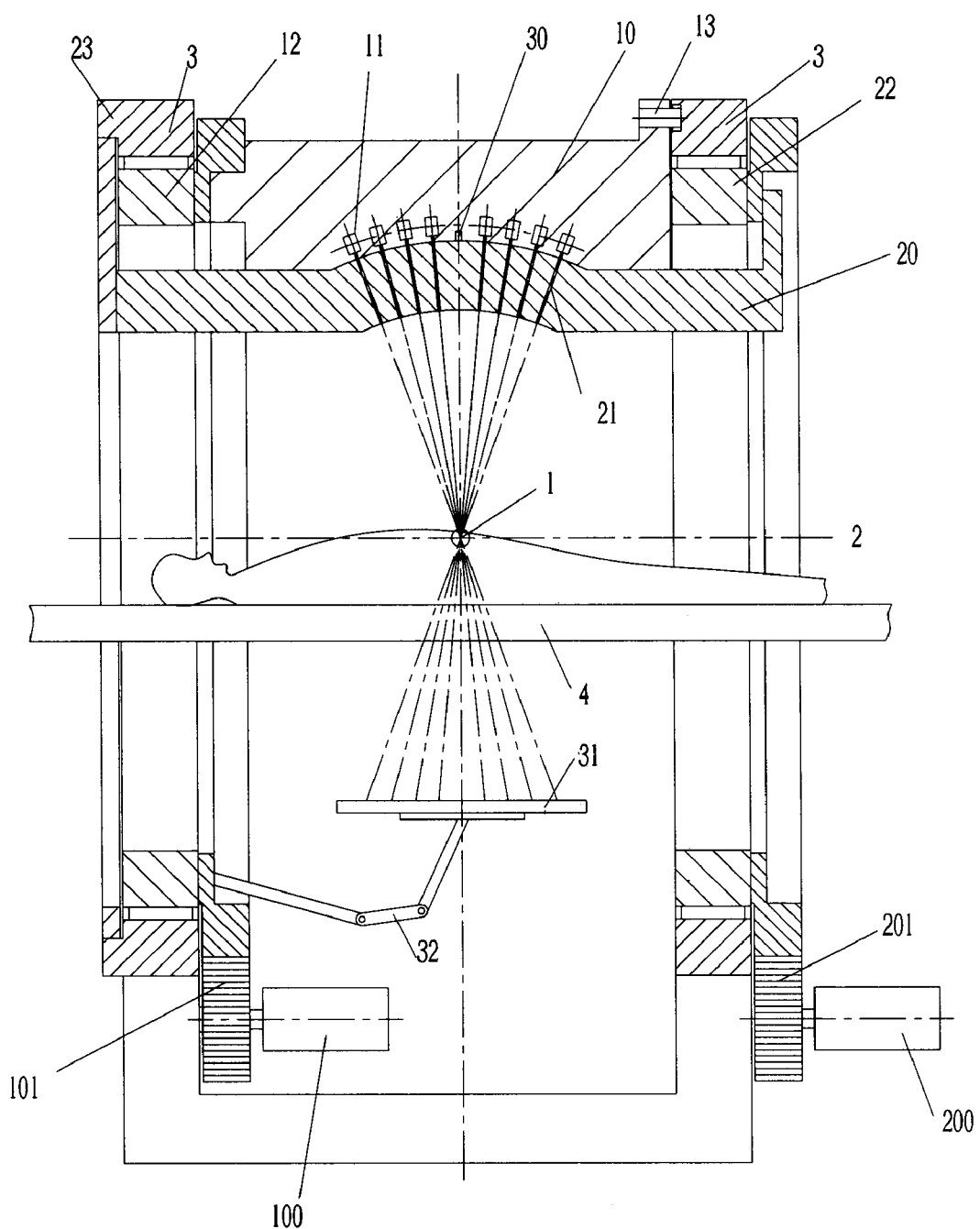
FIG. 6 is an overall structural sectional view of the invention under a therapeutic state in third embodiment.

The third embodiment of the invention is as shown in FIG. 6. One end of the collimator carrier 20 is fixed at the rotary ring 22 of the collimator carrier, while the other end at the joint piece 23 of the collimator carrier. The joint piece 23 of the collimator carrier has a ring-form structure, whose outer surface is fitted by slide to the inner circular surface at one end of the frame 3. Other structural characteristics of this embodiment are the same as those of the first embodiment of the invention.

Figure 7:
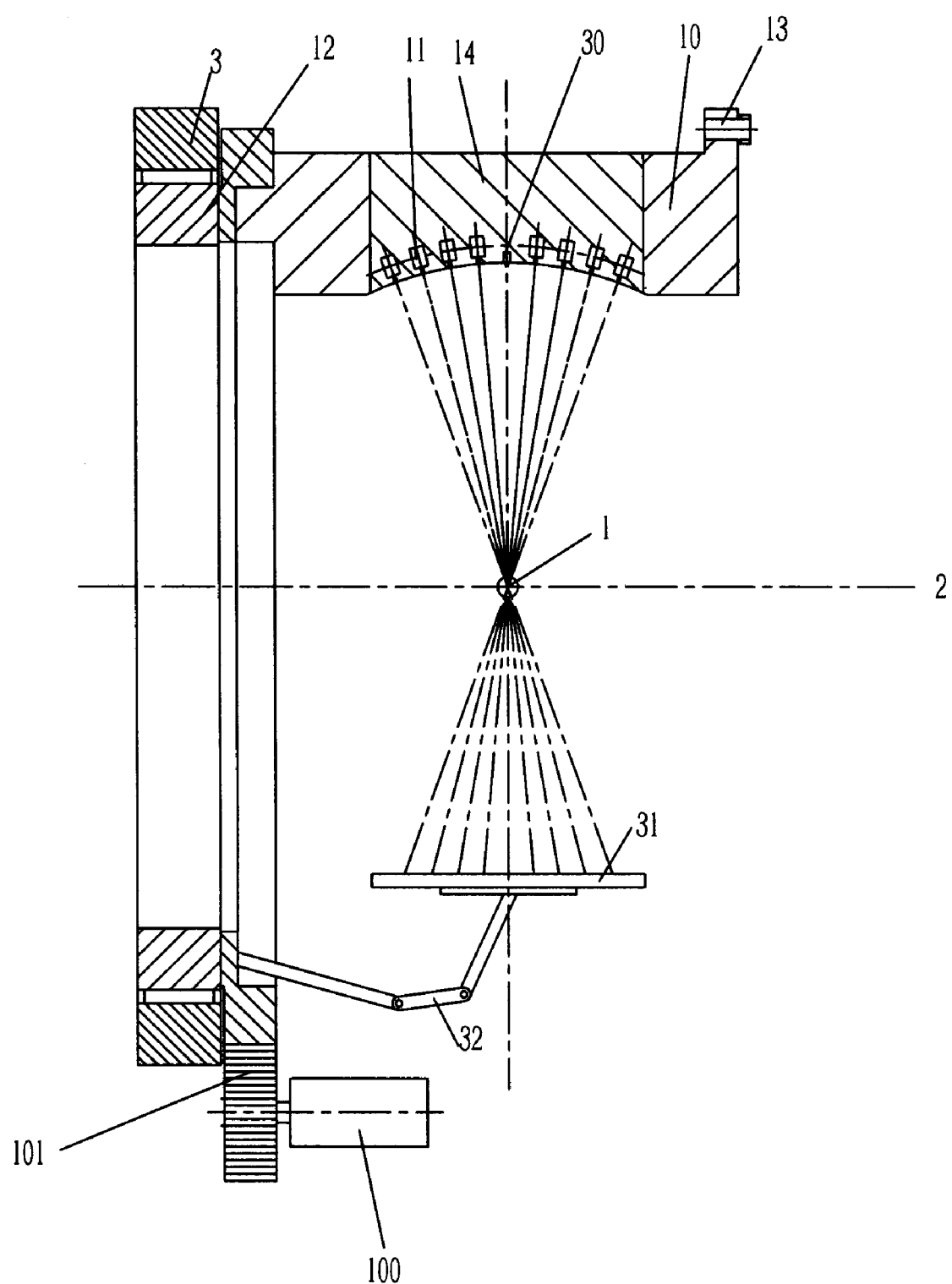
FIG. 7 is a radiation device mechanism diagram of the invention.

As shown in FIG. 7, the radiation device of the invention includes the source carrier 10, the source box 14, the diagnostic radiation sources 30, the therapeutic radiation sources 11, the rotary ring 12 of the source carrier equipped with a gear, the detector 31 connected with the rotary ring 12 of the source carrier through the lever mechanism 32, the actuating device 100 of the source carrier and the transmission piece 101 of the source carrier. One end of the source carrier 10 is connected with the rotary ring 12 of the source carrier, while the other end equipped with a convex block or the joint piece 13 of the source carrier. The source carrier 10 and the detector 31 are oppositely positioned radially along the rotary ring 12 of the source carrier. The source carrier 10 is equipped inside with the demountable source box 14. At source box 14 center, the diagnostic radiation sources 30 are located, and multiple evenly-distributed therapeutic radiation sources 11 along the radial direction are on both sides of radiation source 30. The beam from the radiation sources focuses at the radiation focus 1 at the axis of the source carrier rotary ring 12, and irradiates on the detector 31. The actuating device 100 of the source carrier fixed at the support 3, through the transmission piece 101 of the source carrier and the gear of the rotary ring 12 of the source carrier, drives the rotary ring 12 of the source carrier to rotate around the rotary axis 2, and meanwhile drives the source carrier 10 and the detector 31 to rotate synchronously around the rotary axis 2.

Figure 8:
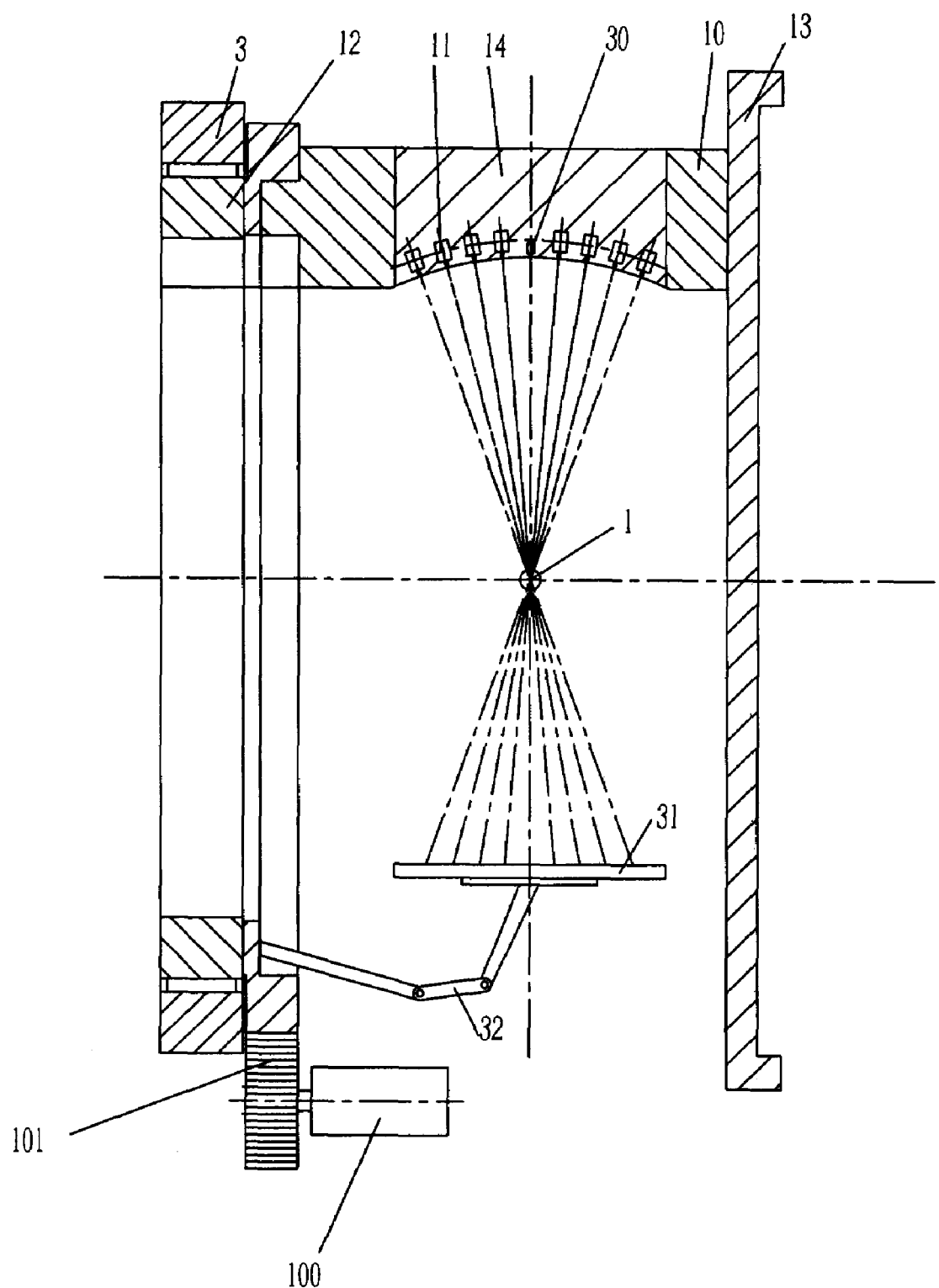
FIG. 8 is a radiation device mechanism diagram of the invention in second embodiment.

The radiation device of the invention for the second embodiment is as shown in FIG. 8. One end of the source carrier 10 is fixed at the rotary ring 12 of the source carrier, while the other end at the joint piece 13 of the source carrier. The joint piece 13 of the source carrier has a ring-form structure with a concave surface. Other structural characteristics of this embodiment are the same as those of the radiation device of the invention for the first embodiment.

What is claimed is:
1. A radiotherapy device comprising:
a frame;
a rotary ring positioned on the frame;
a source carrier and a collimator carrier that can rotate respectively around a rotary axis, the source carrier being equipped inside with multiple radiation sources, the collimator carrier being provided with a corresponding multiple radiation beam channels inside to the radiation sources, which through the channel focus at a radiation focus on the rotary axis;
one end of the source carrier is fixed at the rotary ring of the source carrier while the other end is connected movably with the frame, one end of the collimator carrier is fixed at the rotary ring of the collimator carrier while the other end is connected movably with the frame, the rotary axes of the source carrier and the rotary axes of the collimator carrier rotary ring coincide with each other.

2. The radiotherapy device of claim 1, wherein the rotary ring of the source carrier and the rotary ring of the collimator carrier are coaxial and are positioned on both sides of the radiation focus located at the rotary axis.

3. The radiotherapy device of claim 1, wherein the source carrier and the collimator carrier are connected to frame by rolling fit or slide fit.

4. The radiotherapy device of claim 1, wherein a slip ring is further included, one end of the source carrier and one end of the collimator carrier are fixed respectively at the rotary ring, while the other ends are fixed at the slip ring respectively, the rotary axis of the source carrier and the rotary axis of the rotary ring of collimator carrier coincide with each other.

5. The radiotherapy device of claim 1, wherein the rotary ring is equipped with gears connecting to a power drive mechanism.

6. The radiotherapy device of claim 1, wherein a diagnostic imaging system is further included, comprising diagnostic radiation sources, a detector and a data processing system, the diagnostic radiation sources are positioned in the source carrier while the detector is on the rotary ring of the source carrier, opposite to the diagnostic radiation sources along the rotary axis, the data processing system is connected with the detector, and provides related images of information from the detector.

7. The radiotherapy device of claim 1, wherein a diagnostic imaging system is further included, comprising diagnostic radiation sources, a detector and a data processing system, the diagnostic radiation sources are positioned in the collimator carrier while the detector is on the rotary ring of the collimator carrier, opposite to the diagnostic radiation sources along the rotary axis, the data processing system is connected with the detector, and provides related images of information from the detector.

8. The radiotherapy device of claim 6, wherein the diagnostic radiation sources are cylindrical single photon imaging sources including low activity cobalt-60 radiation sources.

9. The radiotherapy device of claim 6, wherein the detector is connected with the rotary ring through a lever mechanism for moving the detector along the beam of the diagnostic radiation sources.

10. The radiotherapy device of claim 7, wherein the diagnostic radiation sources are cylindrical single-photon imaging sources including low activity cobalt-60 radiation sources.

11. The radiotherapy device of claim 7, wherein the detector is connected with the rotary ring through a lever mechanism for moving the detector along the beam of the diagnostic radiation sources.

* * * * *